United States Patent
Saito et al.

(10) Patent No.: US 7,563,886 B2
(45) Date of Patent: Jul. 21, 2009

(54) NUCLEOSIDE RELEASING FUNCTIONAL UNIT THROUGH OXIDATION AND PROCESS FOR PRODUCING OLIGONUCLEOTIDE CONTAINING THEREOF

(75) Inventors: Isao Saito, Kyoto (JP); Akimitsu Okamoto, Kyoto (JP); Kazuo Tanaka, Kyoto (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 149 days.

(21) Appl. No.: 10/567,364

(22) PCT Filed: Aug. 2, 2004

(86) PCT No.: PCT/JP2004/011039

§ 371 (c)(1),
(2), (4) Date: Feb. 7, 2006

(87) PCT Pub. No.: WO2005/014610

PCT Pub. Date: Feb. 17, 2005

(65) Prior Publication Data

US 2007/0270582 A1 Nov. 22, 2007

(30) Foreign Application Priority Data

Aug. 8, 2003 (JP) ............................. 2003-289972

(51) Int. Cl.
C07H 19/22 (2006.01)
(52) U.S. Cl. ................ 536/27.13; 536/25.32; 536/27.1; 536/27.14
(58) Field of Classification Search ........................ None
See application file for complete search history.

(56) References Cited

U.S. PATENT DOCUMENTS

| 4,774,325 A |   | 9/1988 | Casadio et al. |
| 4,797,480 A | * | 1/1989 | Sorbi et al. ............. 536/26.13 |
| 4,910,300 A | * | 3/1990 | Urdea et al. ............. 536/26.8 |

FOREIGN PATENT DOCUMENTS

| JP | 61-112077 A | 5/1986 |
| JP | 01-500353 A | 2/1989 |
| JP | 2001-270896 A | 10/2001 |

OTHER PUBLICATIONS

Brodelius et al. Eur. J. Biochem. (1974), vol. 47, pp. 81-89.*
English Translation May 18, 2006.
Wu, X. et al., Synthesis and Biological Activity of a Bivalent Nucleotide Inhibitor of Ribonucleotide Reductase, Bioorganic & Medicinal Chemistry Letters, vol. 10, No. 20, pp. 2387 to 2389 (2000).
Okamoto, A. et al., Phototriggered Drug Release from Functionalized Oligonucleotides by a Molecular Beacon Strategy, Angewandte Chemie International Edition, vol. 42, No. 22, pp. 2502 to 2504 (2003).
Ma, Z. et al., "Nucleic acid-triggered catalytic drug release", Proceedings of the National Academy of Sciences of the United States of America, vol. 97, No. 21, pp. 11159 to 11163 (2000).
International Search Report mailed on Sep. 14, 2004.

* cited by examiner

Primary Examiner—Patrick T Lewis
(74) Attorney, Agent, or Firm—Westerman, Hattori, Daniels & Adrian, LLP.

(57) ABSTRACT

A method of easily releasing a useful substance bonded to oligonucleotide without impairing a target nucleic acid; and a novel base therefore. A nucleoside of nucleotide (oligonucleotide containing thereof) represented by the formula (I)

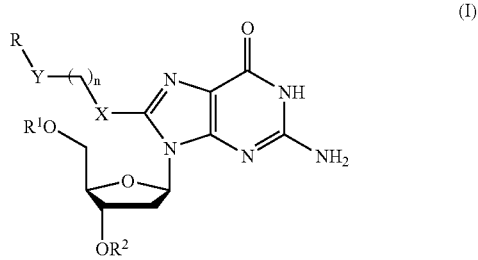

(I)

(wherein each of X and Y independently represents —O—, —NH—, —N(alkyl)- or —S—; R represents a functional unit, a reporter unit or a biofunctional molecule; each of $R^1$ and $R^2$ independently represents a hydrogen atom, a phosphate bond group, a phosphoramidite group or a nucleotide; and n is a numeral of 1 to 10). There is further provided a method of releasing the R group moiety at base portion by the use of the oligonucleotide comprising the nucleotide.

7 Claims, 7 Drawing Sheets

retention time (min)

ODN2: 5'-($^{32}$P)-d(ATTTATAGTGTGGGTTGTTXTTTATTAT)-3'
**ODN2'(U*):** 3'-d(TAAATAU*CACACCCAACAACAAATAATA)-5'
ODN2'(T): 3'-d(TAAATA T CACACCCAACAACAAATAATA)-5'

NUCLEOSIDE RELEASING FUNCTIONAL UNIT THROUGH OXIDATION AND PROCESS FOR PRODUCING OLIGONUCLEOTIDE CONTAINING THEREOF

TECHNICAL FIELD

The present invention relates to a method of releasing a functional unit, a reporter unit or a biofunctional molecule bonded through oxidation to a basic site, as well as a nucleoside or nucleotide therefor or an oligonucleotide containing thereof.

BACKGROUND ART

DNA biosensors have provided a method of extracting necessary information from target genes in a quick and simple manner. For example, various DNA probes that give signals in a sequence-specific fashion, as represented by molecular beacons, have been widely used (see Non-patent Document 1 to 3). However, there are very few DNA probes that can release useful functional molecules (see Non-patent Document 4 to 6).

In a conventional method as a means of releasing a drug from a nucleic acid, photodecomposition of a nitrobenzyl group or a phenacyl group has been utilized. However, molecular design for using a method of introducing a functional molecule by a post-synthesis method is not easy, and a reaction species such as a nitroso group which is harmful to nucleic acid is generated upon release of a drug.

Furthermore, no techniques of removing a fluorescent moiety from fluorescence-modified nucleic acid have been reported.

Non-patent Document 1: Tyagi, S., et al., Nat. Biotechnol., 1996, 14, 303-308
Non-patent Document 2: Tyagi, S., et al., Nat. Biotechnol., 1998, 16, 49-53
Non-patent Document 3: Piatek, A. S., et al., Nat. Biotechnol., 1998, 16, 359-363
Non-patent Document 4 Ma, Z., et al., Proc. Natl. Acad. Sci. USA, 2000, 97, 11159-11163
Non-patent Document 5: Ma, Z., et al., Med. Chem., 2001, 9, 2501-2510
Non-patent Document 6: Okamoto, A., et al., Angew. Chem. Int. Ed., 2003, 42, 2502-2504

DISCLOSURE OF THE INVENTION

A system capable of releasing a specific molecule by external stimulation such as oxidation and photoirradiation is an extremely useful means in gene analysis and for therapy and diagnosis of various diseases.

The present invention provides a method wherein a useful substance (e.g. a dye or a drug) bound to an oligonucleotide can be easily released without impairing a target nucleic acid, and by this release, the substance can be introduced into a target moiety, as well as a novel base therefor.

By using the nucleoside described above and an oligonucleotide containing thereof, a functional unit can be released from the nucleic acid by external stimulation such as photoirradiation and treatment with oxidant. Accordingly, a drug or a reporter molecule can be released from a specific nucleic acid sequence, and a label can be attached to or detached from the nucleic acid, thus making it possible to expect the following: 1) decomposition of a label after use in fluorescent dye- or radioactive substance-labeled nucleic acid and regeneration of the nucleic acid into a gene or the like., 2) gene sensors for detecting an objective nucleotide sequence or one-base polymorphism, 3) drug delivery DNA for regulating gene expression such as replication of DNA, transcription into RNA and recognition of protein, and 4) application to output signals of DNA nano-wires (molecular logical circuit, biosensor etc.).

The inventors have designed a drug-releasing nucleoside based on the mechanism of guanine decomposition by hole generation. The inventors examined a method of modifying the 8-position of guanine and found that basic site of the nucleotide which easily generates holes than natural guanine, in other words, oxidizes easily, can be obtained by bonding a molecule to be released and guanine to each other via a heteroatom.

That is, the present invention relates to a nucleoside, a nucleotide or an oligonucleotide containing thereof represented by the following formula (I)

(I)

(wherein X and Y independently represent —O—, —NH—, —N(alkyl)- or —S—; R represents a functional unit, a reporter unit or a biofunctional molecule; $R^1$ and $R^2$ independently represent a hydrogen atom, a phosphate bonding group, a phosphoramidite group or a nucleotide; and n is a number of 1 to 10.)

The present invention also relates to a method of releasing the R group moiety at the basic site by using an oligonucleotide containing the nucleotide of the invention described above.

The inventors produced a guanine derivative having guanine substituted at the 8-position with a heteroatom. As a group having the heteroatom to be introduced into the 8-position, ethylenediamine was used. An example of this production is as follows:

1

A compound (1) protected with a 4,4'-dimethoxytrityl (DMTr) group at the 5'-position of 8-bromoguanine was treated with ethylenediamine to give a guanine derivative (2) having an ethylenediamino group introduced into the 8-position. This product was trifluoroacetylated with trifluoroacetic acid to afford a compound (3) having a protected N-terminal amino group, which was then converted into a compound (4) wherein the amino group at the 2-position was protected with a dimethylaminomethylidene group, and then bound by a cyanophosphoramidite method (for example, through a compound (5)) etc. to another nucleotide to afford an oligonucleotide, followed by removing the protective groups from the N-terminal amino group at the 8-position and the amino group at the 2-position, whereby an oligonucleotide (6) containing a guanine derivative (hereinafter abbreviated as $^{eda}$G) having an ethylenediamino group at the 8-position could be obtained.

Various kinds of molecules were introduced into the terminal amino group of this ethylenediamine-modified guanine derivative to give N-modified $^{eda}$G In the above reaction formula, the oligonucleotide (7) modified with an acyl group R—CO— is shown. For example, benzoyl-$^{eda}$G can be obtained by acylating the oligonucleotide (6) with benzoic succinimidyl ester.

The inventors conducted photooxidization of the oligonucleotide (7) containing benzoyl-$^{eda}$G ($^{Bz-eda}$G), for example, 5'-d(TATAAT$^{Bz-eda}$GTAATAT)-3'. When this single-stranded oligonucleotide (ODN) was irradiated at 366 nm in the presence of riboflavin, this oligonucleotide (ODN) was rapidly decomposed ($t_{1/2}$=6.2 minutes). As a result of mass spectrometric analysis of the decomposition product in this reaction, it was found that this photooxidization had proceeded as shown in the following reaction formula:

That is, the photodecomposition proceeded at the site of $^{Bz\text{-}eda}$G, and at this site, the purine ring moiety and sugar chain were cleaved, resulting in formation of a decomposition product (8) at the 5'-end, a decomposition product (9) at the 3'-end and a benzamide derivative (10). Such decomposition was considered as previously reported decomposition via a cation radical of guanine, resulting in release of the benzamide derivative (10).

Figure 1:
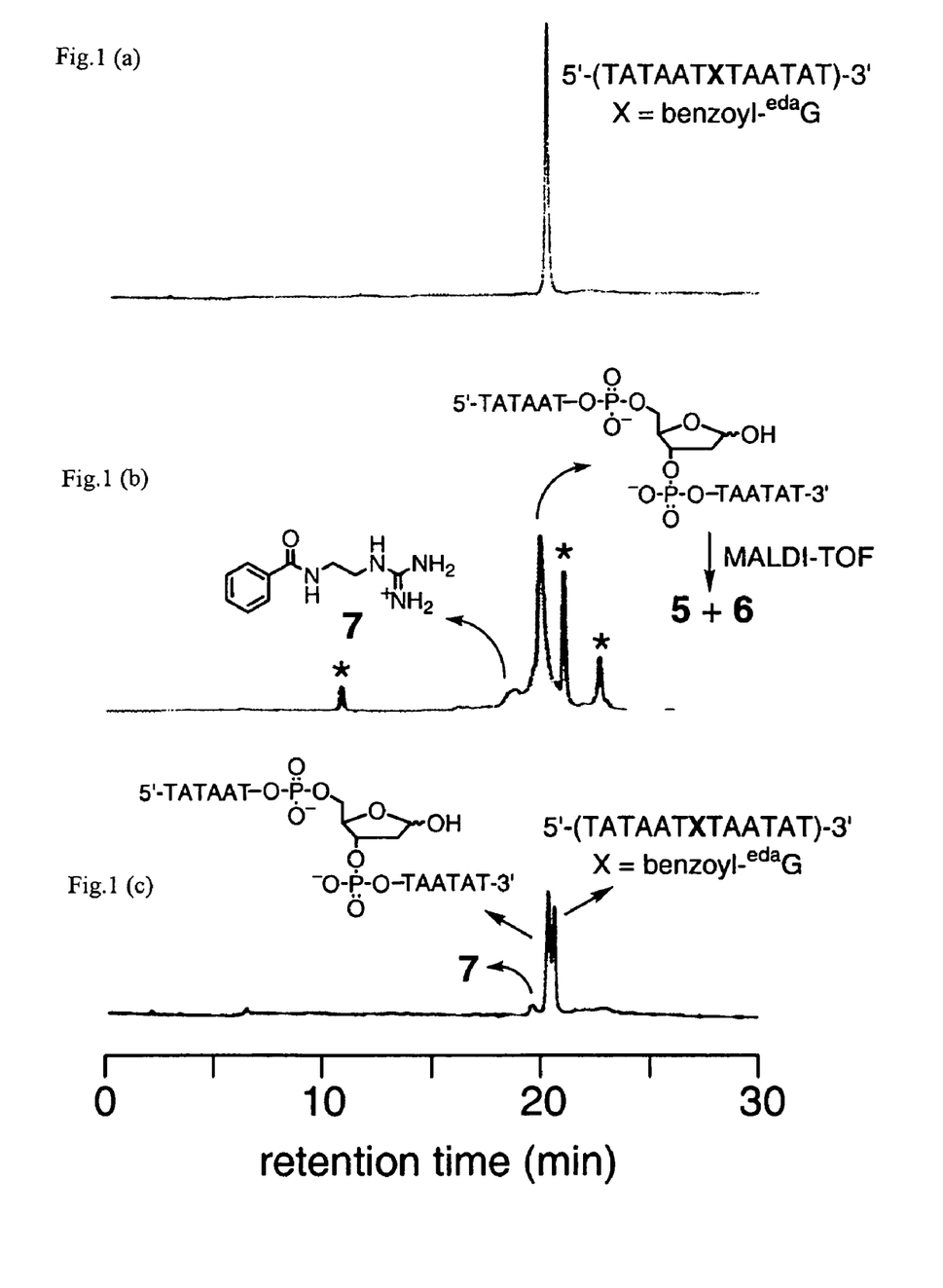
FIG. 1 shows HPLC profiles of decomposition products of the single-stranded oligonucleotide (ODN) of the invention by photoirradiation.

HPLC profiles of this single-stranded oligonucleotide (ODN) by oxidation are shown in FIG. 1. FIG. 1(a) is a HPLC profile of the single-stranded oligonucleotide (ODN) as the starting material, and FIG. 1(b) is a HPLC profile of the decomposition products by photoirradiation. FIG. 1(c) is a HPLC profile of the decomposition products by oxidation with iridium which will be described later.

Figure 2:
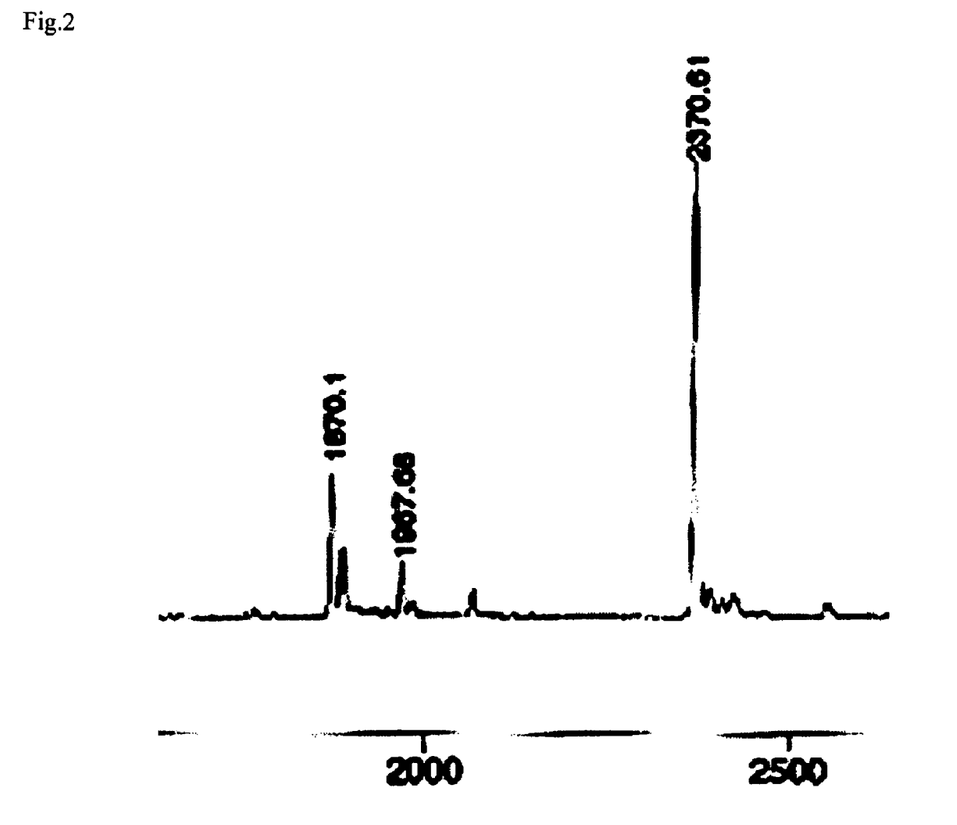
FIG. 2 shows an MALDI-TOF profile of decomposition products of the single-stranded oligonucleotide (ODN) of the invention by photoirradiation.
Figure 3:
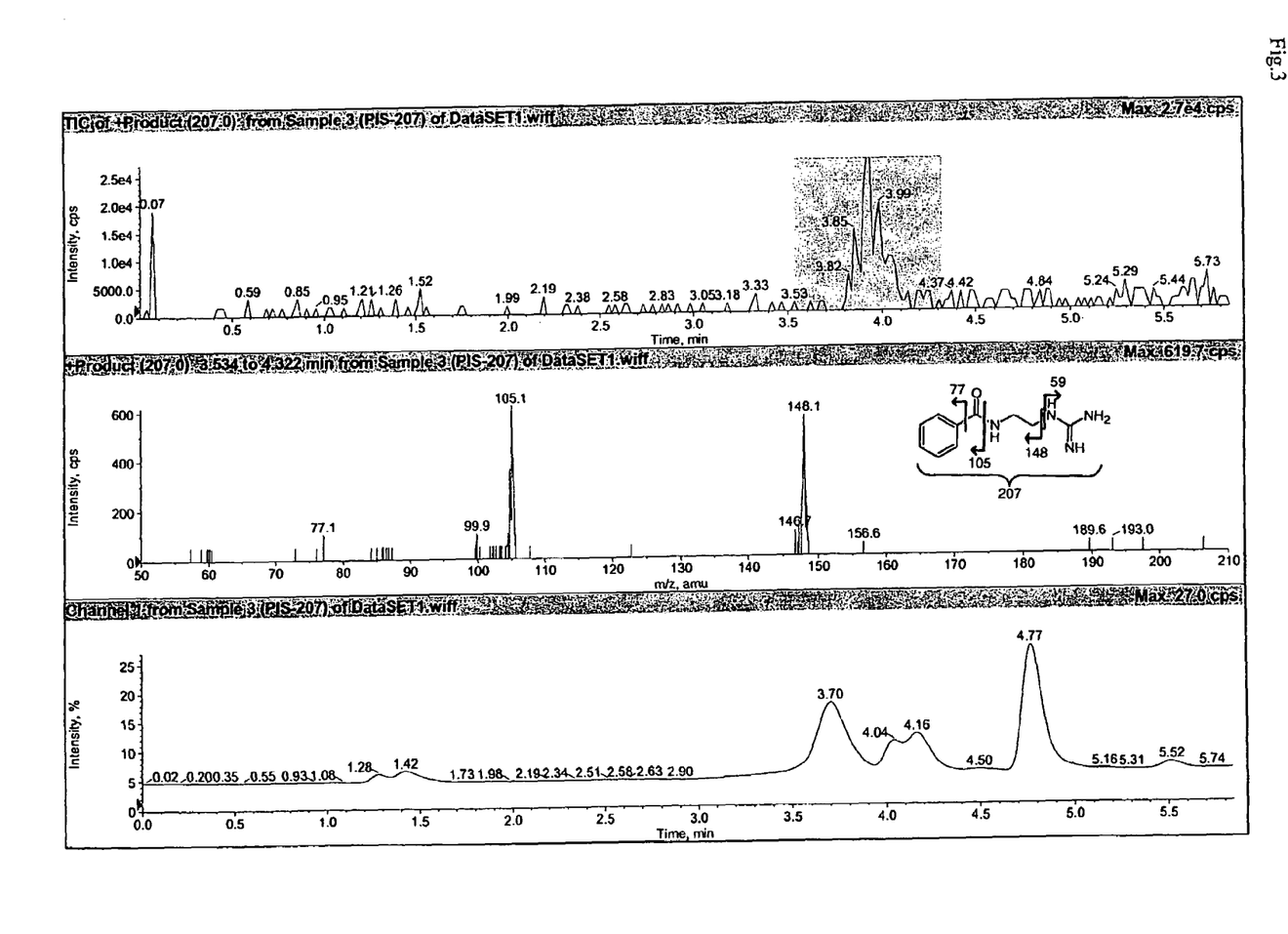

FIG. 2 shows an MALDI-TOF profile of the decomposition products by photoirradiation. In FIG. 2, the peak of 2370.61 is a peak of the starting oligonucleotide used as an internal standard. The peak of 1967.68 is attributable to the decomposition product (8) at the 5'-end, and the peak of 1870.11 to the decomposition product (9) at the 3'-end. FIG. 3 shows the analysis results of the photoirradiated single-stranded oligonucleotide (ODN) by LC-ESI/MS/MS. The upper profile of FIG. 3 is an eluate containing MS207, the middle profile shows fragmentation of MS207, and the lower profile shows an elution pattern in liquid chromatography on Intack C-18 column (2.0×50 mm).

The oxidation potential ($E_{1/2}$) of this $^{Bz\text{-}eda}$G was 0.59 V (vs. NHE). This oxidation potential was close to 0.58 to 0.75 which is the oxidation potential of 8-oxo-guanine (Hickerson, R. P., et al., J. Am. Chem. Soc., 1999, 121, 9423-9428).

It is reported that 8-oxo-guanine and 8-oxo-adenine are site-specifically oxidized with iridium(IV) (Muller, J. G., et al., Nucleic Acids Res., 1998, 26, 2247-2249). Accordingly, 5'-d(TATAATXTAATAT)-3' (X represents $^{Bz\text{-}eda}$G or tetramethylrhodamine (TAMRA)-$^{eda}$G) was oxidized with sodium-hexachloroiridate(IV). As a result, both the oligonucleotides were rapidly decomposed at the site of the modified $^{eda}$G (the site of X) by 57% and 89%, respectively, in 15 minutes.

Figure 4:
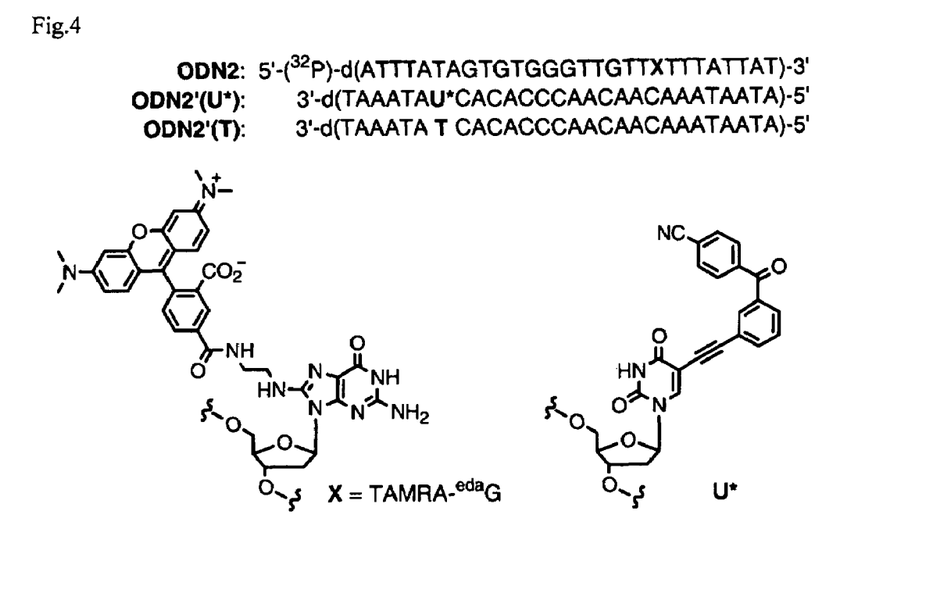
FIG. 4 is shows an outline of the oligonucleotide containing TAMRA-$^{eda}$G in the invention and an outline of its complementary chain.

Then, the inventors examined long-range hole transport. Accordingly, they used an oligonucleotide containing tetramethylrhodamine (TAMRA)-$^{eda}$G, that is, 5'-Q$^{32}$P)-d(ATT-TATAGTGTGGGTTGTTXTTTATTAT)-3' (X represents a tetramethylrhodamine (TAMRA)-$^{eda}$G; hereinafter, this oligonucleotide is referred to as "ODN1"). As its complementary chains, the following chains were produced: 3'-d(TAAATATCACACCCAACAACAAATAATA)-5' (hereinafter, this oligonucleotide is referred to as "ODN2(T)") and an oligonucleotide thereof wherein cyanobenzophenone-modified uridine as a hole injector was introduced in place of thymine (T) at the 7-position, that is, 3'-d(TAAATAU*CACACCCAACAACAAATAATA)-5' (hereinafter, this oligonucleotide is referred to as "ODN2(U*)"). These oligonucleotides are shown in FIG. 4.

Figure 5A:
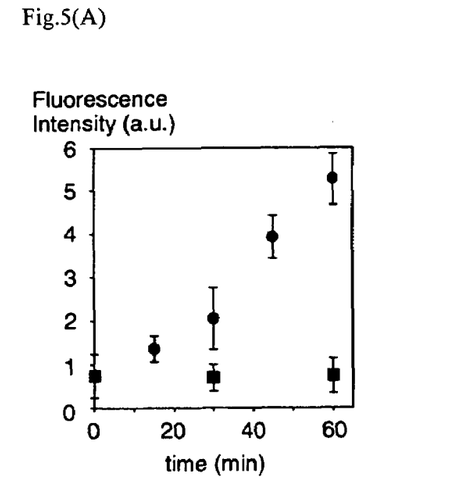
FIG. 5 shows the fluorescence intensity of the double-stranded DNAs of the invention, that is, ODN1/ODN2(T) and ODN1/ODN2(U*) irradiated at 312 nm (FIG. 5(A)) and the cleavage of the oligonucleotides (FIG. 5(B)).

The double-stranded DNAs, that is, ODN1/ODN2(T) and ODN1/ODN2(U*) were irradiated respectively at 312 nm. From these oligonucleotides, photodecomposition products were separated through a centrifugation filter (Micron YM-3) and fluorescence at 576 nm was observed. Strong fluorescence could be observed from the filtrate of ODN1/ODN2 (U*). After irradiation for 60 minutes, the fluorescence measured in the filtrate of ODN1/ODN2(U*) was about 7 times stronger than that in the filtrate of the control ODN1/ODN2 (T). The results are shown in FIG. 5(A). In FIG. 5(A), the black circle (●) is ODN1/ODN2(U*), and the black square (■) is ODN1/ODN2(T). In FIG. 5(A), fluorescence intensity (a.u.) is shown on the ordinate, and the time of photoirradiation (min.) is shown on the abscissa.

Figure 5B:
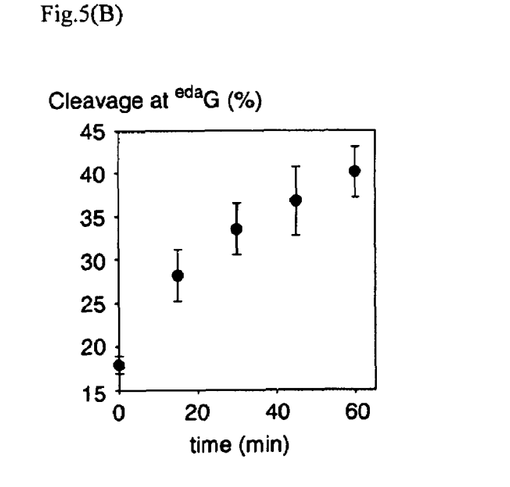
Figure 6:
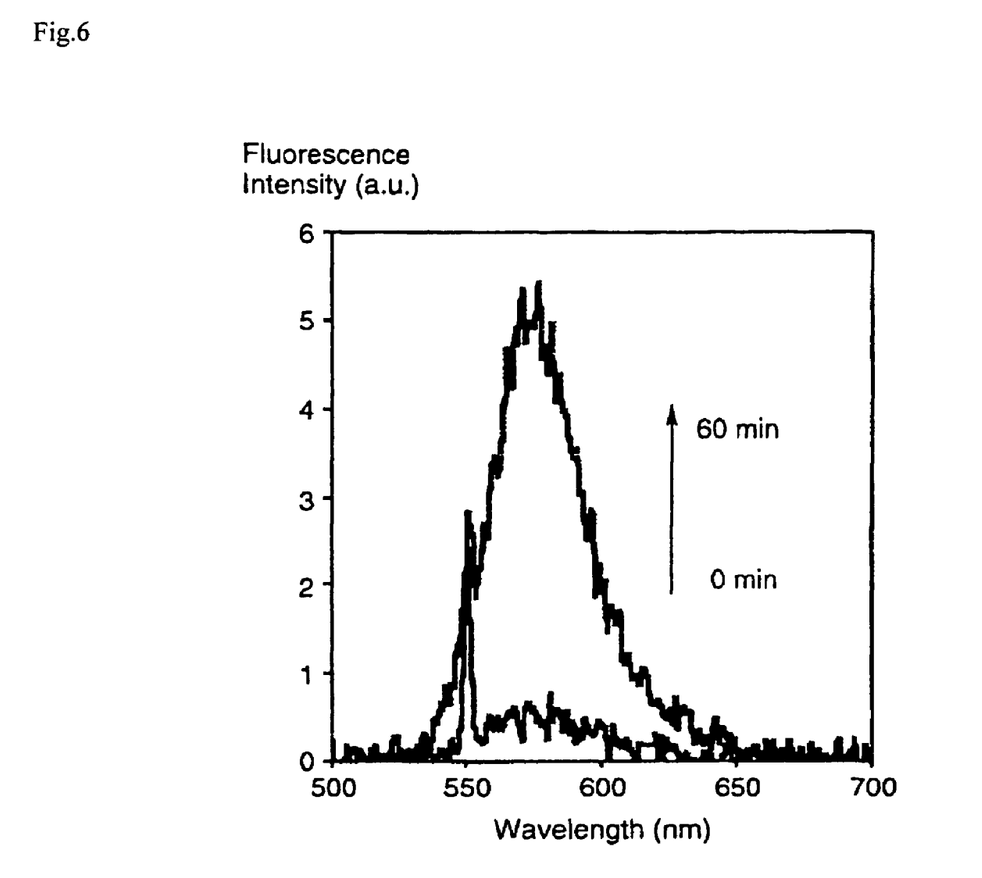
FIG. 6 shows a change in fluorescence intensity of the double-stranded DNA of the invention, ODN1/ODN2(U*), upon irradiation at 312 nm.

The cleavage of ODN1/ODN2(U*) at the $^{eda}G$ site was examined by PAGE. The results are shown in FIG. 5(B). In FIG. 5(B), the cleavage (%) is shown on the ordinate, and the time of photoirradiation (min.) is shown on the abscissa. FIG. 6 shows a change in fluorescence intensity of the double-stranded DNA ODN1/ODN2(U*) upon irradiation at 312 nm. In FIG. 6, fluorescence intensity (a.u.) is shown on the ordinate, and wavelength (nm) is shown on the abscissa.

From the foregoing, it was revealed that the change in fluorescence intensity showed very good correlation with the cleavage of the oligonucleotide at the $^{eda}G$ site. In addition, PAGE analysis revealed that the GGG site at the 5'-end is hindered by photoirradiation.

Figure 7:
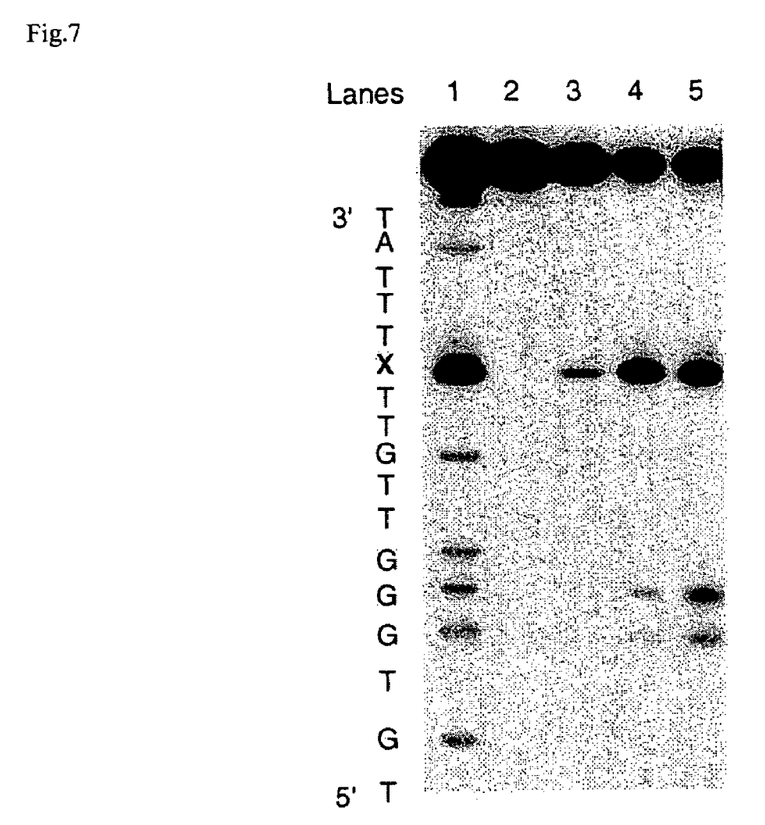
FIG. 7 shows PAGE analysis results of decomposition products of the double-stranded DNA of the invention, ODN1/ODN2(U*), upon irradiation at 312 nm.

FIG. 7 shows PAGE analysis results of the decomposition products of the double-stranded DNA, ODN1/ODN2(U*), upon irradiation at 312 nm. After irradiation, ODN was heat-treated in 50 μL of 10% piperidine (v/v) at 90° C. for 20 minutes. In FIG. 7, X is TAMRA-$^{eda}G$. In FIG. 7, lane 1 is G+A sequence by the Maximum-Gilbert method, lane 2 is full-length ODN1, lane 3 is ODN1/ODN2(U*) just after irradiation, lane 4 is ODN1/ODN2(U*) after irradiation for 30 minutes, and lane 5 is ODN1/ODN2(U*) after irradiation for 60 minutes.

This indicates that a hole generated at the U* site of the double-stranded chain by photoirradiation is transferred to the site of $^{eda}G$ through the double-stranded chain. From the foregoing, it is estimated that the fluorescence of the filtrate of the sample in the initial stage originated from decomposition of $^{eda}G$ mediated to long-range hole transport.

Figure 8:
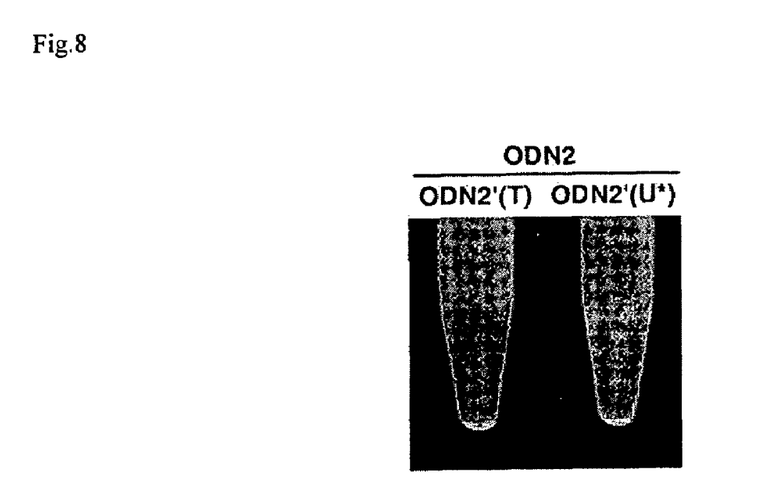
FIG. 8 is a photograph substituted for a drawing, showing a result of visual observation of fluorescence as a result of irradiation at 312 nm of ODN1/ODN2(T) (left side in FIG. 8) and ODN1/ODN2(U*) (right side in FIG. 8) that are the double-stranded DNAs of the invention.

The fluorescence from the photoirradiated sample can also be observed visually. The results are shown in a photograph in FIG. 8 substituted for a drawing. The left side in FIG. 8 shows the fluorescence of the sample from ODN1/ODN2(T), and the right side shows the florescence of the sample from ODN1/ODN2(U*). Strong fluorescence was observed in the sample from ODN1/ODN2(U*) in the right side in FIG. 8, while fluorescence was hardly observable in the sample from ODN1/ODN2(T) in the left side in FIG. 8.

By introducing the guanine derivative such as TAMRA-$^{ed}$ which has a fluorescence-emitting molecule to be decomposed to serve as a reporter unit into a double-stranded DNA, it makes it possible to detect hole transport through DNA without conducting PAGE analysis.

As described above, it was revealed that the guanine derivative having a molecule bound at the 8-position to a heteroatom of the present invention releases the bound molecular species by oxidation, that is, by donation of an electron. The present invention provides the guanine derivative and an oligonucleotide containing thereof. Release of the molecular species from the guanine derivative of the present invention is induced by relatively mild oxidation, and release of such molecular species is extremely useful not only for gene analysis by release of a fluorescent tag but also for a vector releasing a drug in a specific site in vivo.

The guanine derivative having a molecule bound at the 8-position to a heteroatom of the present invention has a structure consisting of a releasable molecular species-heteroatom or an atomic group-purine ring, and is represented preferably by the general formula (I) above.

The —X—(CH$_2$)$_n$—Y— moiety in the general formula (I) corresponds to a linker part for linking a purine ring with a molecular species to be released, and by the presence of a heteroatom, decomposition of guanine is induced to cause release of the bounded molecular species. Accordingly, the linker part is not particularly limited insofar as it contains a heteroatom capable of decomposing guanine and can fix the molecular species to be released, but the linker part is preferably the one mentioned in the general formula (I) above. In the formula (I), X and Y independently represent the same or different heteroatom such as —O—, —NH—, —N(alkyl)- or —S—. In —N(alkyl)-, the alkyl group may be a linear or branched alkyl group having 1 to 10 carbon atom(s), preferably 1 to 5 carbon atom(s) such as a methyl group, ethyl group and n-propyl group. n represents an integer of 1 to 10, preferably 1 to 5, but —(CH$_2$)$_n$— may not always be a linear alkylene group and may be a branched alkylene group. The alkylene group may be an alkylene group in which one or two or more methylene groups are substituted by heteroatoms such as an oxygen atom and a nitrogen atom.

In the general formula (I), the —X—(CH$_2$)$_n$—Y— moiety includes the above-mentioned —NH—(CH$_2$)$_2$—NH— group etc.

The R group in the formula (I) represents the part of a molecular species released through oxidation, and may be any group which upon release, is capable of exhibiting functions possessed by the molecular species. In this specification, the molecular species capable of expressing functions is called "functional unit". Such "functional unit" includes a color-fluorescing unit, a linking molecule such as avidin, a reporter unit functioning as a reporter of an antigen or an antibody, and a biofunctional molecule such as a pharmaceutical preparation or an antibody which regulates biological functions in vivo. For example, when a pharmaceutical preparation is used as the "functional unit", the oligonucleotide used hybridizes with a specific gene, so the oligonucleotide is localized in cells expressing specific mRNA etc., and by oxidant or by photoirradiation, the pharmaceutical preparation can be selectively released at that site, thereby serving as a site-selective DDS preparation.

Each of R$^1$ and R$^2$ in the formula (I) represents a linking group in the sugar moiety of a nucleoside, and R$^1$ and R$^2$ is respectively a hydrogen atom in the case of a nucleoside, but may be a phosphate bonding group for forming a nucleotide or may be a protective group or a phosphoramidite group used as an intermediate of a nucleotide.

The compound represented by the general formula (I) in the present invention may be an oligonucleotide, and said oligonucleotide may contain the above-described modified guanine derivative having a molecular species to be released. Such oligonucleotide of the present invention has at least one modified guanine derivative having a molecular species to be released, and may have two or more modified guanine derivatives, if necessary. In this case, R$^1$ and R$^2$ in the formula (I) represent various nucleotides. Such nucleotide may have one or more bases.

The oligonucleotide of the present invention may be very long, and although the length is not particularly limited, it preferably contains 10 to 100 bases, more preferably 10 to 50 bases.

The oligonucleotide of the present invention does not require a particular electron-donating group, although an oligonucleotide wherein at least one base functioning as an electron-donating group is preferable. Additionally, as described above, since the modified guanine of the present invention can be decomposed even by long-range hole transport, the oligonucleotide of the present invention may also preferably be a double-stranded oligonucleotide in which at least one base in a complementary chain contain an electron-donating group.

Further, the present invention also provides a method of releasing the R group moiety in the nucleotide moiety represented by the formula (I) by oxidizing the oligonucleotide of the present invention.

Figure 9:
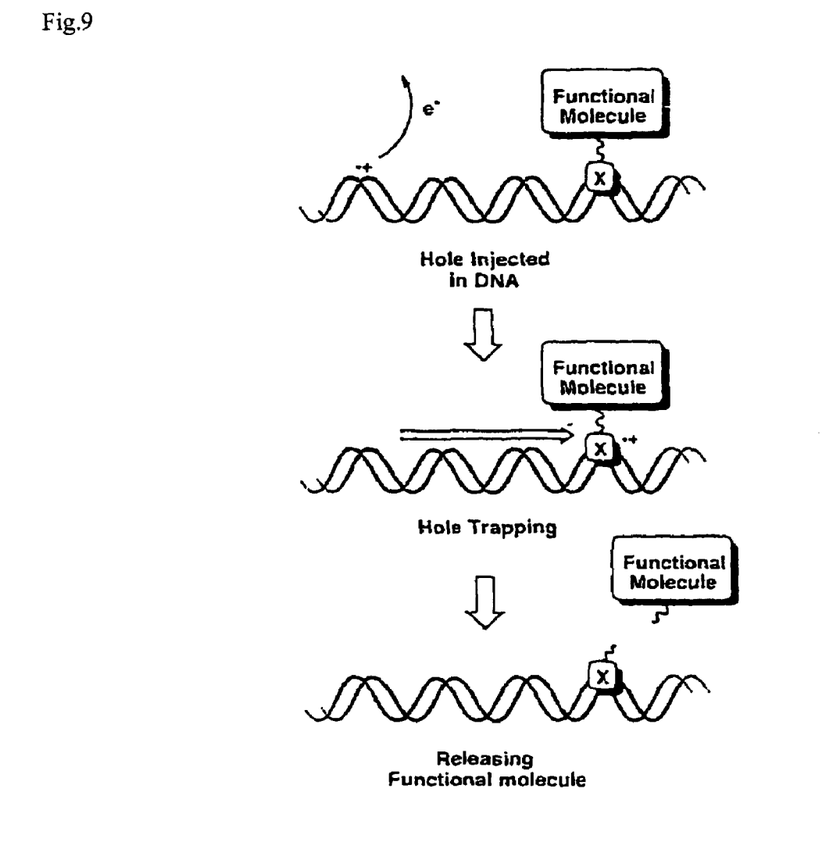
FIG. 9 schematically illustrates release of a functional unit from the oligonucleotide in the method of the present invention.

The outline of release of the R group moiety in the present invention is shown in FIG. 9. FIG. 9 illustrates that a functional unit is bound to the X moiety, and a hole is generated by release of one electron which transfers by long-range hole transport to the X moiety, and the functional unit in the X moiety is released from the oligonucleotide.

Figure 10:
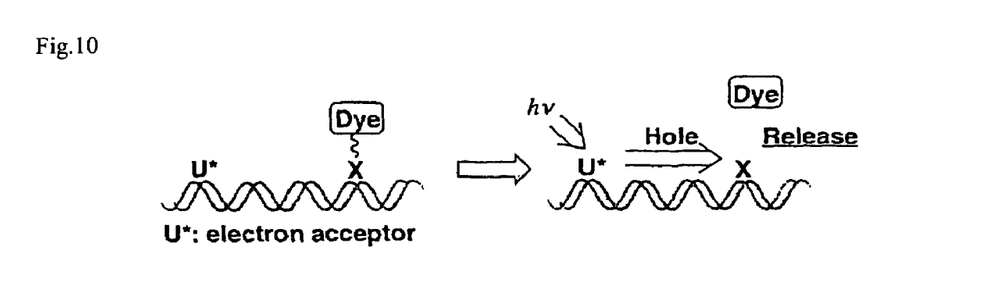
FIG. 10 schematically illustrates release of a dye molecule as a functional unit from the oligonucleotide in the method of the present invention.

FIG. 10 illustrates a release of a dye molecule as a functional unit from the oligonucleotide in the method of the present invention.

The oxidation in this method of the present invention may be relatively mild oxidation and includes, for example, one-electron donation, oxidation by photoirradiation, and oxidation with iridium(IV) or Os(III).

With the nucleotide of the present invention incorporated into the oligonucleotide, introduction of functional unit by formation of an amide or ester linkage, or decomposition of the oligonucleotide by mild oxidation including photoirridiation to release the functional unit is facile. Accordingly, various functional units can be introduced regardless of conditions for synthesizing nucleic acid, and the functional unit can be cleaved off from the oligonucleotide in a desired stage. Use of the nucleotide of the invention in removal of a fluorescence site after fluorescence measurement such as fluorescence in situ hybridization, in release of a drug in a target sequence and in decomposition of a used labeled oligonucleotide can be expected. As an oxidization means for releasing the functional unit, photooxidation with a dye such as riboflavin, oxidation with a metal oxidant such as Ir(IV) or Os(III), or enzyme oxidation with horseradish peroxidase is feasible.

BRIEF DESCRIPTION OF THE DRAWINGS

FIG. 1(a) is a HPLC profile of the single-stranded oligonucleotide (ODN) as the starting material, and FIG. 1(b) is a HPLC profile of the decomposition products by photoirradiation. FIG. 1(c) is a HPLC profile of the decomposition products by oxidation with iridium.

In FIG. 2, the peak of 2370.61 is a peak of the starting oligonucleotide is used as an internal standard. The peak of 1967.68 is assigned to the decomposition product (8) at the 5'-end, and the peak of 1870.11 is assigned to the decomposition product (9) at the 3'-end.

FIG. 3 shows the analysis results of the photoirradiated single-stranded oligonucleotide (ODN) of the invention by LC-ESI/MS/MS. The upper profile of FIG. 3 is an eluate containing MS207, the middle profile shows fragmentation of MS207, and the lower profile shows an elution pattern in liquid chromatography on Intack C-18 column (2.0×50 mm).

In FIG. 5(A), the black circle (●) is ODN1/ODN2(U*), and the black square (■) is ODN1/ODN2(T). In FIG. 5(A), fluorescence intensity (a.u.) is shown on the ordinate, and the time of photoirradiation (min.) is shown on the abscissa. In FIG. 5(B), the cleavage (%) is shown on the ordinate, and the time of photoirradiation (min.) is shown on the abscissa.

In FIG. 6, fluorescence intensity (a.u.) is shown on the ordinate, and wavelength (nm) is shown on the abscissa.

In FIG. 7, X is TAMRA-$^{eda}$G. In FIG. 7, lane 1 is G+A sequence by the Maximum-Gilbert method, lane 2 is full-length ODN1, lane 3 is ODN1/ODN2(U*) just after irradiation, lane 4 is ODN1/ODN2(U*) after irradiation for 30 minutes, and lane 5 is ODN1/ODN2(U*) after irradiation for 60 minutes.

BEST MODE FOR CARRYING OUT THE INVENTION

Hereinafter, the present invention is described in more detail by reference to the Examples, but the present invention should not in the least be limited by Examples below as reference.

EXAMPLE 1

Production of Compound 2

A solution of 8-bromo-5'-O-(4,4'-dimethoxytrityl)-2'-deoxyguanosine (compound (1)) (2.0 g, 30.8 mmol) in ethylenediamine (100 mL) was stirred under reflux at 130° C. for 7 hours. After concentration and drying, a crude product (2) was obtained as brown oily residues.

EXAMPLE 2

Production of Compound 3

In the presence of 10 mL ethyl trifluoroacetate and 25 mL triethylamine, the compound (2) obtained in Example 1 was stirred at 0° C. for 2 hours in 50 mL methanol. After concentration and drying, the process proceeded to the following stage.

EXAMPLE 3

Production of 8-[2-(N-trifluoroacetylamino)ethyl]
amino-2-(N,N-dimethylaminomethylidenyl)amino-
5'-O-(4,4'-dimethoxytrityl)-2'-deoxyguanosine
(Compound (4))

N,N-Dimethylformamide (25 mL) and N,N-dimethylformamide dimethyl acetal (25 mL) were added to the residues obtained after concentration in Example 2, and the reaction solution was stirred at room temperature for 2 hours. After concentration, the residues were purified by silica gel column chromatography (chloroform:methanol=30:1) to give a compound 4 (1.5 g, 63%).

$^1$H NMR (CDCl$_3$) δ: 9.77 (brs, 1H), 9.56 (brs, 1H), 8.54 (s, 1H), 7.34-7.19 (m, 8H), 6.83-6.80 (m, 5H), 6.48 (dt, 1H, J=8.0, 4.0 Hz), 5.83 (brs, 1H), 4.75 (d, 1H, J=5.8 Hz), 4.07 (d, 1H, J=2.4 Hz), 3.765 (s, 3H), 3.763 (s, 3H), 3.76-3.72 (m, 2H), 3.38 (d, 1H, J=8.4 Hz), 3.10 (s, 3H), 3.02 (s, 3H), 3.01-2.95 (m, 2H), 2.80-2.60 (m, 3H), 2.33 (dd, 1H, J=13.3, 8.0 Hz); $^{13}$C NMR(CDCl$_3$) δ: 158.92, 158.91, 158.60, 157.56, 157.19, 156.55, 151.00, 143.55, 139.43, 134.61, 134.57, 130.29, 129.10, 128.42, 128.04, 127.82, 127.73, 127.55, 127.05, 120.27, 117.41, 114.55, 113.30, 113.27, 113.14, 87.01, 85.74, 82.80, 77.21,71.87, 62.87, 55.27, 55.23, 42.65, 41.30, 40.77, 38.73, 35.11;
MS (FAB,NBA/CH$_2$Cl$_2$) m/z(%)779[(M+H)$^+$]; HRMS (FAB) Calcd. for C$_{38}$H$_{42}$N$_8$O$_7$F$_3$[M+H]$^+$]: 779.3129, Found: 779.3128.

EXAMPLE 4

Production of 3'-(O-cyanoethyl-N,N-diisopropylphoshoramidite)-8-[2-(N-trifluoroacetylamino)
ethyl]amino-2-(N,N-dimethylaminomethylidenyl)
amino-5'-O-(4,4'-dimethoxytrityl)-2'-
deoxyguanosine (Compound 5)

A solution of 2-cyanoethyl tetraisopropyl diphosphoramidite (31 µL, 98.9 µmol) and tetrazole (7 mg, 98.9 µmol) in acetonitrile (900 µL) was added to a solution of the compound (4) (70 mg, 89.9 µmol) obtained in Example 3, and then stirred at room temperature for 2 hours. After the precipitated salt (compound (5)) was filtered off, the filtrate was used as such in the subsequent stage.

EXAMPLE 5

Synthesis and Properties of
Oligodeoxyribonucleotide (ODN)

Using Applied Biosystems 392 DNA/RNA synthesizer, an oligodeoxyribonucleotide was synthesized by the conventional phosphoramidite method. The oligodeoxyribonucleotide was subjected to reverse phase high performance liquid chromatography [5-ODS-H column (10×150 mm), elution with a linear acetonitrile gradient (5% to 20%/30 min or more) containing 0.1 M triethyl ammonium acetate (TEAA) (pH 7.0) at a flow rate of 3.0 mL/min]. 50 U/mL calf intestine alkali phosphatase (ALP), 0.15 U/mL snake venom phosphodiesterase (SVPD) and 50 U/mL P1 nuclease were added to a fraction of the purified ODN and reacted at 37° C. for 3 hours to digest the ODN completely. The resulting enzyme digest was analyzed with high performance liquid chromatography (HPLC) [Cosmosil 5C-18AR or CHEMCOBOND 5-ODS-H column (4.6×150 mm), elution with a linear acetonitrile gradient (0% to 20%/20 min or more) containing 0.1 M triethyl ammonium acetate (TEAA) (pH 7.0) at a flow rate of 1.0 mL/min]. The concentration of each ODN was determined by comparison with peaks of a standard solution containing dA, dC, dG and dT at a concentration of 0.1 mM respectively. Properties of each ODN were analyzed with MALDI-TOF MS.

5'-d(TATAAT$^{eda}$GTAATAT)-3': Calcd. for m/z [M−H]$^-$: 4028.72, Found: 4027.33;
5'-d(ATTTATAGTGTGGGTTGTT$^{eda}$GTTTATTAT)-3': Calcd. for m/z [M−H]$^-$: 8732.69, Found: 8732.87.

EXAMPLE 6

60 nM oligonucleotide (6) obtained in Example 5 was incubated at 5° C. for 16 hours in 500 µL of 50 mM phosphate buffer (pH 7.0) containing 50 µL of 1 mg/mL solution of an objective functional molecule succinimidyl ester (for example benzoic succinimidyl ester or the like) in dimethyl sulfoxide, whereby a functional oligonucleotide (7) was obtained.

EXAMPLE 7

Photooxidation Reaction of the Single-stranded
Oligonucleotide

The single-stranded oligonucleotide (ODN) 5'-d (TATAAT$^{eda}$GTAATAT)-3' was irradiated at 366 nm in the presence of riboflavin. As a result, this oligonucleotide (ODN) was rapidly decomposed (t$_{1/2}$=6.2 minutes).

The HPLC results are shown in FIG. 1. The results of mass spectrometric analysis of the decomposition products are shown in FIGS. 2 and 3.

Decomposition Product (8)(MALDI-TOF)
5'-TATAAT-OPO$_3$—CH$_2$—CH(OH)—CH=CH—CHO: Calcd. for [M−H]$^-$; 1968.32, Found: 1967.68;

Decomposition Product (9) (MALDI-TOF)
$^-$O—PO$_3$-TAATAT-3': Calcd. for [M−H]$^-$; 1870.22, Found: 1870.11;

Decomposition Product (10) (LC-ESI/MS/MS)
Calcd. for [C$_{10}$H$_{15}$ON$_4$]$^+$: M$^+$ 207. Fragments: 148, 105, 77, 59.

EXAMPLE 8

Measurement of Oxidation Potential (E$_{1/2}$) of
Benzoyl-$^{eda}$G

The oxidation potential (E$_{1/2}$) of benzoyl-$^{eda}$G was measured in 100 mM LiClO$_4$ solution at room temperature by ALS electrochemical analyzer model 660-A. The scanning speed was 100 mV/sec. A glass carbon electrode was used as a sample electrode; a platinum wire as a counter electrode; and SCE as a reference electrode. The result indicated that the oxidation potential (E$_{1/2}$) of benzoyl-$^{eda}$G was 0.59 V (vs. NHE).

EXAMPLE 9

Example of Decomposition of ODN1/ODN2(T) and
ODN1/ODN2(U*) when Irradiated Respectively at
312 nm The oligonucleotide having a base concentration of 1 mM in 50 mM sodium cacodylate buffer (pH 7.0) containing 50

μM one-electron oxidizing agent riboflavin was irradiated with light at 366 nm by a trans-illuminator. It was recognized that 90% of the oligonucleotide was decomposed by irradiation for 1 minute, and almost all of the oligonucleotide was decomposed by irradiation for 5 minutes. The oligonucleotide was decomposed into nucleotide units by enzyme decomposition and was analyzed, it was revealed that the oligonucleotide was decomposed and disappeared in the position of the modified nucleoside only.

The results are shown in FIGS. 5 to 8.

The invention claimed is:

1. A nucleoside, a nucleotide or an oligonucleotide, comprising:
a moiety represented by the following formula (I):

(I)

wherein X and Y each represent —NH—;
wherein R represents a color-fluorescing unit, a reporter unit or a biofunctional molecule;
wherein $R^1$ and $R^2$ each represent a hydrogen atom, a phosphate bonding group, a phosphoramidite group or a nucleotide; and
wherein n is 2.

2. The nucleoside, the nucleotide or the oligonucleotide according to claim 1, wherein R represents a color-fluorescing unit.

3. The oligonucleotide according to claim 1, wherein the oligonucleotide contains 10 to 100 bases.

4. The oligonucleotide according to claim 3, wherein the oligonucleotide is double-stranded and contains at least one base having an electron-donating group in a complementary chain.

5. A method of releasing an R group moiety in a nucleotide moiety, said method comprising:
oxidizing an oligonucleotide moiety,
wherein said oligonucleotide moiety is represented by the following formula (I):

(I)

wherein X and Y each represent —NH—;
wherein R represents a color-fluorescing unit, a reporter unit or a biofunctional molecule;
wherein $R^1$ and $R^2$ each represent a hydrogen atom, a phosphate bonding group, or a phosphoramidite group; and
wherein n is 2.

6. The method according to claim 5, wherein the oxidization is one-electron donation.

7. The method according to claim 5, wherein the oxidization is by photoirradiation.

* * * * *

```
                          SEQUENCE LISTING

<160> NUMBER OF SEQ ID NOS: 4

<210> SEQ ID NO 1
  <211> LENGTH: 28
  <212> TYPE: DNA
  <213> ORGANISM: Artificial Sequence
  <220> FEATURE:
  <223> OTHER INFORMATION: Chemically Synthesized
  <220> FEATURE:
  <221> NAME/KEY: misc_feature
  <222> LOCATION: (20)..(20)
  <223> OTHER INFORMATION: n means TAMRA-edaG.

<400> SEQUENCE: 1
atttatagtg tgggttgttn tttattat                                           28

<210> SEQ ID NO 2
  <211> LENGTH: 28
  <212> TYPE: DNA
  <213> ORGANISM: Artificial Sequence
  <220> FEATURE:
  <223> OTHER INFORMATION: Chemically Synthesized
  <220> FEATURE:
  <221> NAME/KEY: misc_feature
  <222> LOCATION: (22)..(22)
  <223> OTHER INFORMATION: n means 4'-cyanobenzophenone-3-ilacetylenil-
        uracil.

<400> SEQUENCE: 2
ataataaaca acaacccaca cnataaat                                           28

<210> SEQ ID NO 3
  <211> LENGTH: 28
  <212> TYPE: DNA
  <213> ORGANISM: Artificial Sequence
  <220> FEATURE:
  <223> OTHER INFORMATION: Chemically Synthesized
  <220> FEATURE:
  <223> OTHER INFORMATION: ODN2(T)

<400> SEQUENCE: 3
ataataaaca acaacccaca ctataaat                                           28

<210> SEQ ID NO 4
  <211> LENGTH: 28
  <212> TYPE: DNA
  <213> ORGANISM: Artificial Sequence
  <220> FEATURE:
  <223> OTHER INFORMATION: Chemically Synthesized
  <220> FEATURE:
  <221> NAME/KEY: misc_feature
  <222> LOCATION: (19)..(19)
  <223> OTHER INFORMATION: n means T-eda

<400> SEQUENCE: 4
atttatagtg tgggttgtng tttattat                                           28
```